US006924138B2

(12) United States Patent
Lockhart

(10) Patent No.: US 6,924,138 B2
(45) Date of Patent: Aug. 2, 2005

(54) SINGLE- AND MULTI-MODE CONFIGURATIONS FOR FIBER-OPTIC-COUPLER BIOSENSORS

(75) Inventor: Michael D. Lockhart, Charlottesville, VA (US)

(73) Assignee: Veridian Systems Division, Charlottesville, VA (US)

( * ) Notice: Subject to any disclaimer, the term of this patent is extended or adjusted under 35 U.S.C. 154(b) by 686 days.

(21) Appl. No.: 10/095,733

(22) Filed: Mar. 12, 2002

(65) Prior Publication Data

US 2002/0127707 A1 Sep. 12, 2002

Related U.S. Application Data

(60) Provisional application No. 60/274,967, filed on Mar. 12, 2001.

(51) Int. Cl.$^7$ ................................................ C12M 1/34
(52) U.S. Cl. ................ 435/287.1; 385/11; 385/12; 385/15; 385/27; 385/28; 385/30; 385/31; 385/39; 385/42; 385/43; 356/318; 356/364; 422/82.05; 422/82.11; 435/287.2; 435/288.7; 435/808; 436/164; 436/165; 436/518; 436/527; 436/805
(58) Field of Search ................ 385/11, 12, 15, 385/27, 28, 30, 31, 39, 42, 43; 356/318, 364; 422/82.05, 82.11; 435/287.1, 287.2, 288.7, 808; 436/164, 165, 805, 518, 527

(56) References Cited

U.S. PATENT DOCUMENTS 5,494,798 A    2/1996  Gerdt et al. ................ 435/6

6,103,535 A  *  8/2000  Pilevar et al. ................ 436/518

* cited by examiner

Primary Examiner—Christopher L. Chin
(74) Attorney, Agent, or Firm—Gifford, Krass, Groh, Sprinkle, Anderson & Citkowski, PC

(57) ABSTRACT

Single-mode and multi-mode fibers to achieve modal splitting and greater sensitivity in an optical fiber coupler for evanescent-wave biosensor applications. A source of light having multiple modes is coupled to the input to one of the multi-mode fibers, with the geometry of necked-down section being such that a limited number of modes may be carried by the multi-mode fiber as the light emerges from the coupler. At least one of the single-mode fibers is supported adjacent the multi-mode fiber to receive and carry one of the limited modes. A biomolecule enveloped by the evanescent field, exhibits a direct or indirect affinity to a binding partner, such that attachment of the binding partner is at least partially responsible for the limited number of modes carried by the multi-mode fiber as the light emerges from the coupler. A system-level implementation of the invention further includes instrumentation for receiving the light from the single-mode fiber carrying one of the limited modes, and determining a characteristic of the binding partner in accordance with the detected mode. The attachment of the binding partner may also causes a change in other detectable optical attributes, such as the magnitude or polarization of the light at one or both of the fiber outputs. The instrumentation may therefore further include a polarization-sensitive optical element supported at one or both of the outputs of the optical fibers, for example, in the form of a polarizing beamsplitter. One or more of the fibers may be pulled substantially without twisting so as to maintain polarization orientation, and the source of light may randomly, circularly, or linearly polarized.

7 Claims, 2 Drawing Sheets

SINGLE-AND MULTI-MODE CONFIGURATIONS FOR FIBER-OPTIC-COUPLER BIOSENSORS

REFERENCE TO RELATED APPLICATION

This application claims priority from U.S. provisional patent application Ser. No. 60/274,967, filed Mar. 12, 2001, the entire contents of which being incorporated herein by reference.

FIELD OF THE INVENTION

This invention relates generally to fiber-optic, evanescent-wave biosensors and, in particular, to alternative optical coupler arrangements for such sensors.

BACKGROUND OF THE INVENTION

Optical fibers are being used in a variety of biosensor applications. For example, as discussed in U.S. Pat. No. 5,494,798, an optical fiber may be used without cladding to exploit the evanescent field present immediately outside the fiber/air interface. If a monoclonal or polyclonal antibody is attached to the exposed surface of the bare fiber, the evanescent field envelopes the molecule. But since there is little or no absorption or other phenomena to alter the amount of the light carried by the fiber, no attenuation or detectable characteristics are developed.

However, when an appropriately labeled antigen is attached to the antibody, the evanescent field can cause the antigen to fluoresce, resulting in an optically detectable characteristic such as a reduction in light intensity or fluorescence. Alternatively, by first binding the antigen, the sensor can used to detect unknown targets, including toxins or immunogenic agents.

Whereas previous fiber-optic evanescent-wave sensors utilized multi-mode fibers, the '798 patent improved on the technique by employing a pair of single-mode optical fibers in a coupler arrangement. Light is introduced into one of the fibers to produce an evanescent region surrounding the coupling area, and the magnitude of light emitted from the pair of fibers is compared for detection purposes.

FIG. 1, taken from the '798 patent, shows the overall fiber optic system generally at 10. Light from laser diode 14 is inserted into a first leg 17 of a fiber optic coupler 18, and exits on the same fiber at 19 (input channel). A second fiber 20 provides an output channel for light from the first leg 17. A first photo diode detector 21 is connected to the input channel and a second photo diode detector 22 is connected to the output channel.

Each detector feeds its own transimpedance amplifier. The outputs of the transimpedance amplifiers 23, 24 are applied to A/D converters 25 and 26 which provide digital electrical signals along wires 27 and 28 to an instrumentation board 29. The instrumentation board 29 is then connected to a personal computer 30 which provides outputs to a printer or a monitor.

The finished probe includes the coupler and attached antibodies, which yields a baseline ratio for the sensor. The finished probe is then exposed to a material of interest, and the ratio of the light through the two sides of the coupler changes as a function of the way in which the target attaches. That is, the localized index of refraction at the coupling region and the determination of the ratio is a function of the binding in the coupler region.

In terms of the coupler itself, existing designs use off-the-shelf components intended for multiplexers and demultiplexers in telecommunications applications. Corning, for instance, makes these couplers by twisting together two or more 1300-nm, single-mode type 9-125 optical fibers, heating up the twisted area and pulling the ends apart to create a necked-down, nearly fused union. The number of fibers and other factors such as the proportion of each fiber in the twisted region determines the coupling ratio.

SUMMARY OF THE INVENTION

In contrast to the prior art, which teaches the use of two identical single-mode, communication grade optical fibers to form an evanescent-wave biosensor, this invention combines single-mode and multi-mode fibers to achieve modal splitting and greater sensitivity.

To form the coupler, at least one multi-mode fiber and at least one single-mode fiber are brought together, heated and pulled to form a necked-down coupler region around which an evanescent field is generated. Each fiber has an input and an output. A source of light having multiple modes is coupled to the input to one of the multi-mode fibers.

In the preferred embodiment, the geometry of necked-down section is such that a limited number of modes may be carried by the multi-mode fiber as the light emerges from the coupler. At least one of the single-mode fibers is supported adjacent the multi-mode fiber to receive and carry one of the limited modes.

A biomolecule enveloped by the evanescent field, exhibits a direct or indirect affinity to a binding partner, such that attachment of the binding partner is at least partially responsible for the limited number of modes carried by the multi-mode fiber as the light emerges from the coupler. A system-level implementation of the invention further includes instrumentation for receiving the light from the single-mode fiber carrying one of the limited modes, and determining a characteristic of the binding partner in accordance with the detected mode.

Numerous biomolecules and binding partner associations may be used, including antigen-antibody, substrate-enzyme, effector-enzyme, inhibitor-enzyme, complimentary nucleic acid strands, binding protein-vitamin, binding protein-nucleic acid, reactive dye-protein, and reactive dye-nucleic acid interactions.

The attachment of the binding partner may also causes a change in other detectable optical attributes, such as the magnitude or polarization of the light at one or both of the fiber outputs. The instrumentation may therefore further include a polarization-sensitive optical element supported at one or both of the outputs of the optical fibers, for example, in the form of a polarizing beamsplitter. One or more of the fibers may be pulled substantially without twisting so as to maintain polarization orientation, and the source of light may randomly, circularly, or linearly polarized.

DETAILED DESCRIPTION OF THE INVENTION

This invention improves upon the prior art by combining single-mode and multi-mode fibers in an optical coupler, for biosensor applications, in particular. Broadly, whereas the disclosure of the '798 patent referenced above teaches the use of two identical single-mode, communication grade optical fibers, this invention prescribes the use of a multi-mode input and a single mode output.

Figure 1:
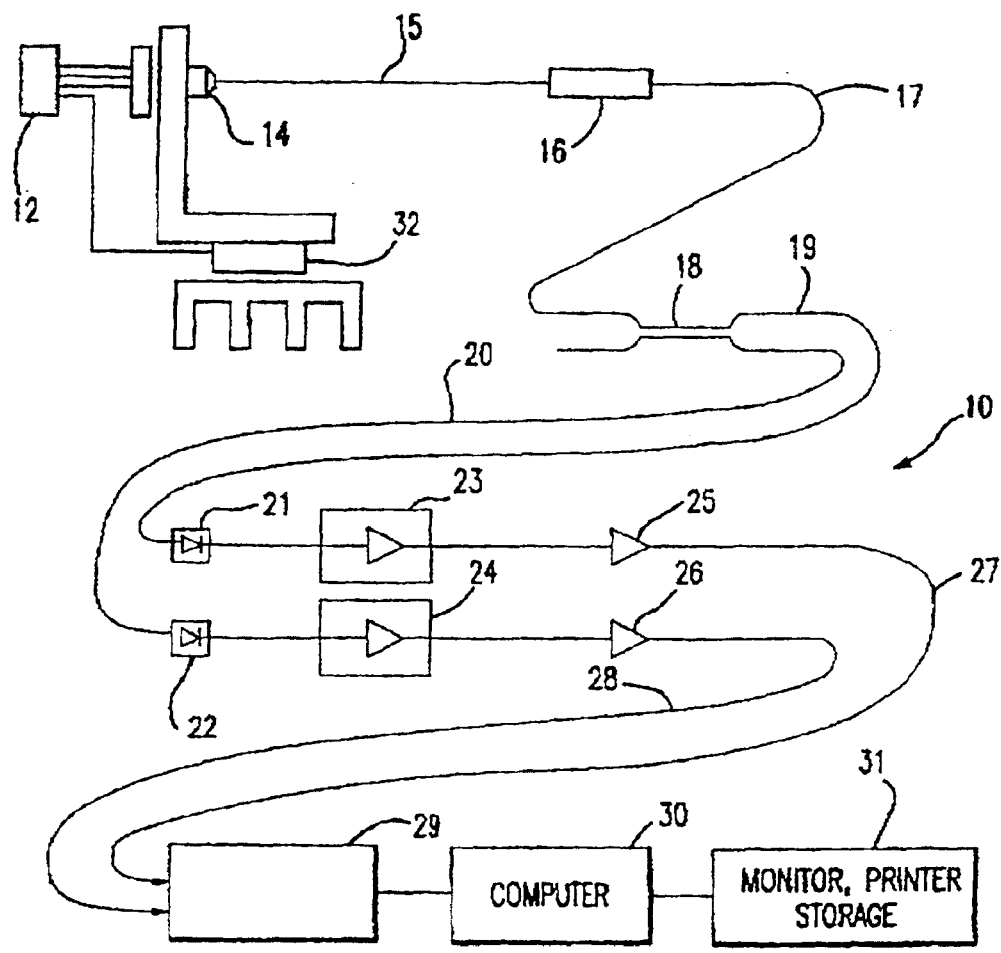
FIG. 1 is a diagram which illustrates a prior-art coupled-fiber evanescent wave biosensor configuration.
Figure 2:
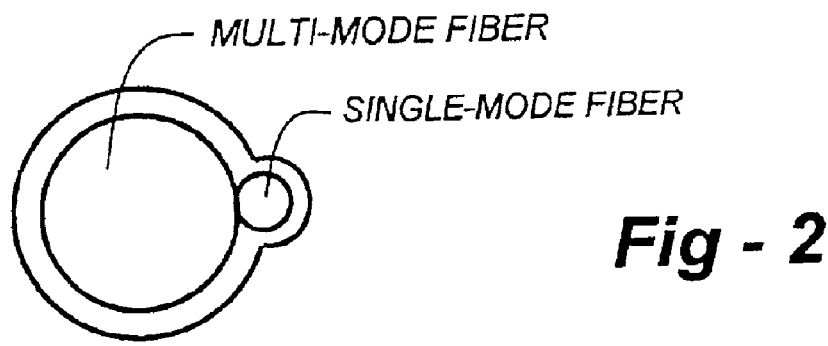
FIG. 2 shows how at least one multi-mode fiber and at least one single-mode fiber are brought together, heated and pulled to form a coupler region according to the invention.

To form the coupler, at least one multi-mode fiber and at least one single-mode fiber are brought together, heated and pulled to form a coupler region. This is depicted in FIG. 2. Interestingly, if the multi-mode fiber is sufficiently necked-down in the sensor region, if operates as a single-mode fiber for the short distance of the coupler region. Although the multiple modes are regenerated when the light emerges from the coupler region, the multi-mode fiber can only carry a single mode out of the coupler region.

Figure 3:
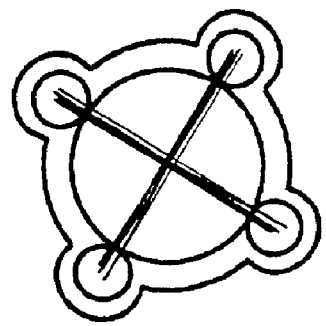
FIG. 3 shows how single-mode fibers may be used to detect a pair of criss-crossed modes.

This invention exploits this phenomenon to perform modal splitting. That is, the mode or modes of light emerging from the output of the fiber may be detected to determine the particular substance bound to the coupler. Advantageously, as opposed to one single-mode fibers, a plurality of single mode fibers may be used to surround a common multi-mode fiber, each with the capability of detecting a different mode coming out of the single mode end of the multi-mode fiber. FIG. 3, for example, shows how single-mode fibers 302 and 304 may be used to detect a pair of criss-crossed modes. It should be apparent that other detection schemes are possible, such as 1×5, 1×8, and so forth wherein, in each case, only certain modes are permitted to physically couple with respect to a given axis based upon the way in which they are configured.

Figure 4:
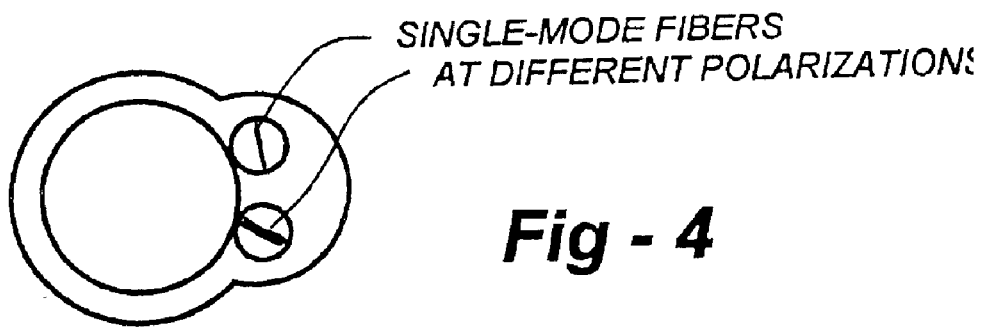
FIG. 4 depicts the use of single-mode omni polarization or polarization-maintaining fibers.

In addition to mode splitting, the invention may take advantage of other optical phenomena such as polarization. This may be achieved, for example, through the use of single-mode omni polarization or polarization-maintaining fibers, as shown in FIG. 4. Using such a configuration, only specific polarizations are allowed to traverse through one or the other types of fibers in the cell. In summary, whereas teachings of the '798 patent are strictly limited to coupling ratio, certain of the embodiments described herein may sense modality, polarization, interferometric or modulation characteristics without actually looking at a ratio in light intensity or magnitude.

APPLICATIONS

This invention provides a sensitive detector having a wide variety of applications in the fields of biology, biochemistry and chemistry, and in many clinical applications. Although the terms "antigen" and "antibody" are used herein, it will be appreciated that is a special case, and that the invention finds utility beyond the more general target-specific molecular recognition. Indeed, the invention is applicable to both direct types of lock-and-key molecular recognition and indirect mechanisms, for example, subclasses of carbohydrates that are based upon more of a pattern match than a precise attachment mechanism.

In broad and general terms, the invention sense a change in one or more optical properties due to chemical/biochemical/bioaffinity/immunogenic-type interactions of biomolecules (ligands) with their respective binding partners. The terms ligand and its binding partner for the ligand or, simply, binder will be used to represent the two components in specific bioaffinity binding pairs, all of which are capable of recognizing and binding with the other partner in a bimolecular recognition pair. References to "biomolecular" or "molecular constituent," "binding partner," and so forth are used interchangeably and are not intended to in any way limit the invention, since the invention is applicable to any type of organic/inorganic material, so long as the interaction of one component causes a change in any optical property detectable by the apparatus. Interactions to which the invention is applicable include, but are not limited to, antigen-antibody, carbohydrate-lectin, receptor-ligand, binding protein-toxin, substrate-enzyme, effector-enzyme, inhibitor-enzyme, complimentary nucleic acid strands, binding protein-vitamin, binding protein-nucleic acid, reactive dye-protein, and reactive dye-nucleic acid interactions.

A molecular constituent useful in the present invention is characterized by an ability to specifically interact with another molecule, the interaction resulting in a change in an optically detectable property. A molecular constituent is any molecule, or portion of a molecule, that is capable of being attached, directly or indirectly to a waveguide such that it is capable of specific interaction with another molecule present in a test sample. Examples of a molecular constituent illustratively include a protein, a peptide, a polysaccharide, a sugar, an antibody, an antigen, a hapten, a receptor, a ligand such as an agonist or antagonist, a sugar binding protein such as a lectin, a toxin, a virus, a bacterium, a cell, a cell component such as an organelle, a particle such as a liposome, a nucleic acid, a drug and a prion. A molecular constituent further includes fragments or metabolites of the listed substances capable of specific interaction as described. Further, a molecule interacting with another molecule of the present invention is a gas illustratively including NO, $O_2$, $CO_2$. A molecular constituent also illustratively includes a chemical-sensitive polymer, a chemical-sensitive microimprinted polymer and a chemical-sensitive dye.

The terms "interaction" and "binding" are used interchangeably herein and refer to a selective association, through chemical or physical means, of two or more molecules. By "selective association" is meant that a first molecule binds preferentially to a second molecule or with greater affinity than to most other molecules. For example, a DNA molecule will selectively associate with a substantially complementary sequence and not with unrelated nucleic acids.

A test sample containing a molecular constituent to be detected is typically a biological sample. A biological sample is obtained from a human or other animal or from an environmental site where the earth, water or air are to be tested. Environmental sites include outdoor locations as well as indoor location such as laboratories, hospitals and manufacturing facilities. A sample illustratively refers to a cells, tissue or physiological fluid, such as plasma, serum, cerebrospinal fluid, saliva, semen, amniotic fluid, tears, milk, and fluids obtained from respiratory, upper digestive, intestinal, and genitourinary tracts. A test sample also includes fluid or a suspension of solids obtained from wounds, tumors and organs. Further, a test sample is obtained to test for environmental contamination. For example, a surface suspected to be contaminated by bacteria is swabbed and the bacteria obtained are suspended in a solution for later introduction into a biosensor of the present invention.

In one embodiment of the present invention, the interaction of molecular constituents acts to cleave or release molecules attached to the waveguide. For example, a substrate is attached to a waveguide and an enzyme to be detected interacts with the substrate under appropriate conditions. The resulting enzyme activity cleaves the substrate causing a change in an optical property.

In an embodiment of the instant invention, the interaction of molecular constituents results in the formation of another molecular species such that a change in an optical property is detected. For example, an enzyme interacts with a substrate to produce a product deposited on or near the waveguide such that a change in an optical property is detected. Techniques of enzymatic reaction are well known in the art. A preferred example is horseradish peroxidase used in conjunction with diaminobenzidine and $H_2O_2$ or a similar substrate such as tetramethylbenzidine or aminoethylcarbazole.

The term "attached" as used herein to describe the relationship of a first molecular constituent with a waveguide is intended to mean attached either directly or indirectly to the waveguide. An illustrative example of a direct attachment is a link to a pendant moiety on a waveguide via a pendant chemical moiety present on the first molecular constituent. An indirect attachment occurs, for example, where a molecular constituent is optionally attached to a waveguide via a linker. Where a linker is used the choice of linker depends on the surface of the waveguide and the molecular constituent to be attached. Selection of an appropriate combination will be evident to one skilled in the art. For example, where the surface has available Si—OH groups, appropriate linkers include aminoalkyltrialkoxysilanes, aminoalkyltrichlorosilanes, carboxyalkyltrialkoxysilanes, epoxyalkyltrialkoxysilanes, hydroxyalkyltrialkoxysilanes and hydroxyalkyltrichlorosilanes. Further suitable silanes are listed in Silicon Compounds: Register & Review, from United Chemical Technologies, 5th Ed., 1991. Further illustrative examples of linkers include aryl acetylene, diamines, diacids, polyalcohols, polyesters, polyethers, polylysine, polyarginine, polystyrene sulfonate, dextran sulfate, chondroitin, polyacrylic acid, polymethacrylic acid, polyacrylamide, polyallylamine, maleic acid, substituted or unsubstituted polyalkylenes, polyamines, polyamides, polysufonates, polyoxides, polyalkyleneglycols, polystyrenic-based polymers, polyacetals, polysaccharides, polycarbonates, polyurethanes, polyureas, polyamides, polyethyleneimines, polyarylene sulfides, polysiloxanes, polyimides, polyacetates, polymers of monoethylenically unsaturated monomers, polymers of polyvinylidene monomers and mixtures and copolymers of the above polymers. Following linker binding, unreacted functional groups on the waveguide surface are optionally blocked to prevent further reaction.

It will be appreciated by one skilled in the art that a molecular constituent attached to a waveguide is removable according to the mechanism of attachment used. Thus, a wave guide according to the invention is reusable.

An apparatus of the present invention allows detection of a molecular constituent in a test sample where the concentration of the constituent is in the range of $10^{-3}$ M to $10^{-15}$ M or less. Sensitivity of the apparatus will depend in part on the amount and concentration of the constituent attached to the waveguide.

Substances are optionally introduced into the cavity 140 to facilitate an interaction between molecular constituents. For example, a gel is introduced into the cavity. Gels operative in the present invention are any that do not interfere with the desired interaction and illustratively include agarose and acrylamide. The viscosity of a gel is chosen such that a molecular constituent in a sample to be tested remains in the cavity available for interaction with the waveguide attached molecular constituent for an appropriate period of time which is apparent to one of skill in the art.

It will be readily apparent to one of skill in the art that specific interaction between molecular constituents is to some extent dependent on appropriate interaction conditions such as temperature, salt concentration and buffer composition. Solutions used in a biosensor apparatus of the present invention are adjusted according to the desired interaction. An apparatus of the present invention optionally has a thermostatic control for regulating the temperature at which the molecular constituents are brought into contact.

The interaction of molecular constituents causing a change in an optical property is not limited to the interaction of two constituents. Thus, interaction of three or more molecules may be required to cause an optical change. For example, an antibody attached to a waveguide interacts with an antigen to be detected resulting in minimal or undetectable change in an optical property. A third molecular constituent, such as an antibody interacts with the antigen-antibody complex to bring about a change in an optical property.

As a final note, although the invention assumes the use of glass fibers, polymeric fibers and other materials may be used, depending upon the wavelengths of interest or other aspects of the particular analytical configuration. Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

I claim:

1. A fiber-optic-coupler biosensor comprising:

a fiber-optic coupler incorporating at least one multi-mode and at least one single-mode optical fibers, each fiber having an input and an output;

a source of light having multiple modes being coupled to the input to one of the multi-mode fibers;

the coupler including a necked-down section around which an evanescent field is generated when the light passes through, the necked-down section being such that a limited number of modes may be carried by the multi-mode fiber as the light emerges from the coupler, and wherein at least one of the single-mode fibers is supported adjacent the multi-mode fiber to receive and carry one of the limited modes;

a biomolecule enveloped by the evanescent field, the biomolecule exhibiting a direct or indirect affinity to a binding partner, such that attachment of the binding partner is at least partially responsible for the limited number of modes carried by the multi-mode fiber as the light emerges from the coupler; and instrumentation for:

a) receiving the light from the single-mode fiber carrying one of the limited modes, and b) determining a characteristic of the binding partner in accordance with the detected mode.

2. The optical biosensor of claim 1, wherein the biomolecule and binding partner include or more of the following:

antigen-antibody, substrate-enzyme, effector-enzyme, inhibitor-enzyme, complimentary nucleic acid strands, binding protein-vitamin, binding protein-nucleic acid, reactive dye-protein, and reactive dye-nucleic acid interactions.

3. The optical biosensor of claim 1, wherein the instrumentation includes a polarization-sensitive optical element supported at one or both of the outputs of the optical fibers.

4. The optical biosensor of claim 3, including a polarization-sensitive optical element in the form of a polarizing beamsplitter.

5. The optical biosensor of claim 1, wherein attachment of the binding partner also causes a change in magnitude of the light at one or both of the fiber outputs.

6. The optical biosensor of claim 1, wherein:

the necked-down section is produced by pulling the optical fibers; and wherein one or more of the fibers are pulled substantially without twisting so as to maintain polarization orientation.

7. The optical biosensor of claim 1, wherein the source of light is randomly polarized.

* * * * *